United States Patent

Nichols et al.

[11] Patent Number: 6,136,864
[45] Date of Patent: *Oct. 24, 2000

[54] DENATURANTS FOR SYMPATHOMIMETIC AMINE SALTS

[75] Inventors: W. Michael Nichols, Fanwood; William Bess, Edison; Stanley Lech, Rockaway, all of N.J.

[73] Assignee: Warner-Lambert Company, Morris Plains, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/937,408
[22] PCT Filed: Apr. 1, 1997
[86] PCT No.: PCT/US97/05509
§ 371 Date: Sep. 25, 1997
§ 102(e) Date: Sep. 25, 1997
[87] PCT Pub. No.: WO97/37689
PCT Pub. Date: Oct. 16, 1997
[51] Int. Cl.⁷ ..................................................... A61K 47/18
[52] U.S. Cl. ............................................ 514/653; 514/305
[58] Field of Search ..................... 514/653, 305; 252/365; 502/185; 564/358

[56] References Cited

U.S. PATENT DOCUMENTS

| | | | |
|---|---|---|---|
| 3,169,092 | 2/1965 | Petraglia et al. | |
| 3,773,920 | 11/1973 | Nakamoto et al. | 424/465 |
| 4,265,875 | 5/1981 | Byrne et al. | 424/436 |
| 4,493,827 | 1/1985 | Valle | 424/720 |
| 4,601,894 | 7/1986 | Hanna et al. | 424/480 |
| 4,657,757 | 4/1987 | Hanna et al. | 424/488 |
| 4,689,223 | 8/1987 | Arias | 424/682 |
| 5,407,686 | 4/1995 | Patel et al. | 424/468 |
| 5,585,108 | 12/1996 | Ruddy et al. | 424/434 |

FOREIGN PATENT DOCUMENTS

| | | |
|---|---|---|
| 9004021 | 2/1991 | South Africa . |
| WO9428870 | 12/1994 | WIPO . |
| WO9608252 | 3/1996 | WIPO . |

OTHER PUBLICATIONS

Aloamaka et al. Effect of Pregnancy on Relaxation of Rat Aorta to Magnesium. Cardiovascular Research. 1993. vol. 27, No. 9. pp. 1629–1633. Abstract Only.

Uncle Fester; Secrets of Methamphetamine Manufacture Fourth Edition; 1996; pp. 154–159.

Table of Cough Cold Products Sold in the United States.

*Primary Examiner*—Robert H. Harrison
*Attorney, Agent, or Firm*—Evan J. Federman; Michael J. Atkins

[57] ABSTRACT

A pharmaceutical composition has an acid salt of a sympathomimetic amine; and a denaturant of (i) at least one gum or viscosity modifier, and (ii) at least one surfactant, wherein the gum or viscosity modifier and the surfactant are present in amounts sufficient to have a denaturing effect on the sympathomimetic amine without significantly compromising the release of the sympathomimetic amine from the composition.

40 Claims, No Drawings

DENATURANTS FOR SYMPATHOMIMETIC AMINE SALTS

FIELD OF THE INVENTION

It is believed that the legal and widely available acid salts of sympathomimetic amines, such as the decongestants pseudoephedrine hydrochloride, pseudoephedrine sulfate, ephedrine hydrochloride and phenylpropanolamine hydrochloride, are being used in the chemical synthesis of illegal drugs such as methamphetamine, amphetamine, methcathinone, and cathinone. This invention, by the incorporation of one or more denaturant compounds, renders commercially available, "over the counter" ("OTC") medications containing sympathomimetic amine salts much less suitable as starting materials in the production of illegal drugs. The denaturant(s) exhibit chemical or physical properties which make the isolation of the pure sympathomimetic amine salt difficult or essentially infeasible from a product containing a combination of the denaturant(s) and the sympathomimetic amine salt. Because the isolation of pure sympathomimetic amine salt is rendered impractical, attempts to use compositions proposed in this invention as a source of starting material for the synthesis of illegal drugs will result in compromised yields of adulterated product.

In one preferred embodiment, the term "denaturant" refers to a compound whose separation from sympathornimetic amine salts is difficult or essentially infeasible, so that the synthesis of illegal drugs from the compositions of the invention is rendered impracticable and/or produces illegal drugs in an adulterated form. In another preferred embodiment, the term "denaturant" refers to materials that physically interfere with the extraction of the sympathomimetic amine salts from the pharmaceutical products (i.e., emulsifies and/or alters viscosity of the pharmaceutical products in solution), so that the purification of the sympathomimetic amine salts from the pharmaceutical products is rendered impractical. The denaturant is understandably pharmacologically and biologically acceptable to mammals due to its presence in OTC medications.

BACKGROUND OF THE INVENTION

2.1 Sympathomimetic Pharmaceuticals

Sympathomimetic compounds, as the name implies, exert biological effects similar to those produced by activation of the sympathetic nervous system. For example, the pharmaceutical compound pseudoephedrine acts as an indirect sympathomimetic agent by causing adrenergic nerve endings to release norepinephrine, thereby stimulating $\alpha$ and $\beta$ norepinephrine receptors, particularly in blood vessels of the upper respiratory tract. This, in turn, results in vasoconstriction and shrinkage of swollen tissues in the sinuses and nasal passages.

2.2. The Problem of Illegal Conversion

Methamphetamine is a powerful and destructive drug sold illegally on the street as "crack, "meth" and "speed". Illegal use of methamphetamine is becoming increasingly common. In California alone, hospitals have seen more than a 300 percent increase in emergency room admissions from methamphetamine abuse in the last ten years.

One of the most efficient starting materials in the synthesis of methamphetamine is ephedrine, which is heavily regulated and therefore difficult to obtain. Increasingly, pseudoephedrine, an enantiomer of ephedrine, is being used in the production of methamphetamines. Pseudoephedrine can be obtained from a pseudoephedrine salt, such as pseudoephedrine hydrochloride, which is a common ingredient in over-the-counter ("OTC") medications.

Pseudoephedrine hydrochloride may be isolated from OTC medications by suspending/dissolving the commercial products in water. The resulting slurry/solution is filtered and then treated with base to neutralize the amine salt, pseudoephedrine hydrochloride, thereby producing pseudoephedrine free base. The free base, which has limited water solubility, is then extracted into a water immiscible solvent such as ether. This extraction serves as a purification step. Acidification to regenerate the amine hydrochloride followed by extraction into water is normally adequate to produce suitably pure pseudoephedrine hydrochloride.

It can be understood that it would be beneficial to prevent or deter illegal conversion of sympathomimetic amine compounds while maintaining OTC availability.

SUMMARY OF THE INVENTION

The present invention is directed to the addition of one or more pharmaceutically and biologically acceptable denaturants to sympathomimetic amine salt-containing pharmaceutical products to make these products less suitable as starting materials for the production of illegal drugs. The denaturant (s) exhibit chemical or physical properties which make the isolation of the pure sympathomimetic amine salt difficult or essentially infeasible from a product containing a combination of the denaturant(s) and the sympathomimetic amine salt. Because the isolation of pure sympathomimetic amine salt is rendered impractical, attempts to use compositions proposed in this invention as a source of starting material for the synthesis of illegal drugs will result in compromised yields of adulterated product.

In one preferred embodiment, the term "denaturant" refers to a compound whose separation from sympathomimetic amine salts is difficult or essentially infeasible, so that the synthesis of illegal drugs from the compositions of the invention is rendered impracticable and/or produces illegal drugs in an adulterated form. In another preferred embodiment, the term "denaturant" refers to materials that physically interfere with the extraction of the sympathomimetic amine salts from the pharmaceutical products (i.e., emulsifies and/or alters viscosity of the pharmaceutical products in solution), so that the purification of the sympathomimetic amine salts from the pharmaceutical products is rendered impractical. The denaturant is understandably pharmacologically and biologically acceptable to mammals due to its presence in OTC medications.

The present invention is directed to denaturant-containing sympathomimetic amine products and to methods for their preparation. The denaturant-containing sympathomimetic amine products are used for known indications treated by sympathomimetic amines.

DETAILED DESCRIPTION OF THE INVENTION

For clarity of description, and not by way of limitation, the detailed description of the invention is divided into the following subsections: i) denaturants; ii) sympathomimetic amines; and iii) compositions.

Denaturants

As used herein, the term "denaturant" refers to a compound which has (i) a physical property which renders its separation from a sympathomimetic amine difficult or essentially infeasible and/or (ii) a chemical property which interferes with illegal sympathomimetic amine-based drug synthesis.

Differential solubility in various solvents is a physical property that may complicate or preclude the separation of a denaturant from a sympathomimetic amine. For example, the isolation of sympathomimetic amines from OTC preparations generally comprises the steps of (i) dissolving the OTC preparation in aqueous solution; (ii) filtering; (iii) adding base to produce the relatively water insoluble, hydrophobic free base form of the sympathomimetic amine; (iv) filtering the precipitate free base; (v) extracting the remaining free base into lipophilic solvent; (vi) evaporating the solvent; and (vii) dissolving the free base in acid to regenerate the acid salt of the sympathornimetic amine. A denaturant having similar solubility's during each of these steps would be difficult or impossible to separate from sympathomimetic amine. Depending on the chemical structure of the denaturant, it may or may not be substantially altered by the addition of base or acid or by exposure to aqueous or lipophilic solvents. What is desirable is that at each step of the purification process, the solubility of the denaturant (in whatever form) parallels that of the sympathomimetic amine. Solubility may be quantified by means of solubility constants for particular solvents, for example, as set forth in The Handbook of Chemistry and Physics, 77th edition, copyright 1996. In particular non-limiting embodiments, the solubility constant for the denaturant at each step of the purification process may vary from the solubility constant of the sympathomimetic amine by ±50 percent or less, preferably ±30 percent or less, more preferably ±20 percent or less, and still more preferably ±10 percent or less. These variances may differ from step to step of the purification process.

Alternatively, the denaturant may have physical properties which differ from that of the sympathomimetic amine but that nevertheless render the purification of sympathomimetic amine difficult to achieve. For example, the denaturant may be a substance which is sparingly soluble in aqueous solution such that compositions comprising both denaturant and sympathomimetic amine are difficult to dissolve (e.g., denaturant—coated particles comprising sympathomimetic amine, and sympathomimetic amine embedded in a denaturant matrix).

In other embodiments of the invention a denaturant may have one or more chemical properties that interfere with illegal drug synthesis. Such interference may occur at any one or several steps of either the purification of sympathomimetic amine or its conversion into an illegal drug. The terms "interfere" and "interference" refer to an impedance of the purification and/or conversion process as a result of a chemical reaction involving the denaturant. For example, chemical reaction of denaturant may produce a product compound which is nontoxic but which may have an unpleasant taste, smell, emetic effect, etc. Alternatively, the presence of denaturant may exhaust reactants intended to be directed toward sympathomimetic amne, thereby decreasing the efficiency of purification and/or conversion.

The amount of a denaturant extracted along with the sympathornimetic amine salt may be assessed analytically. When the extraction method is that commonly chose by known "meth cooks" (i.e. free base sympathornimetic amine extracted from water into a water immiscible solvent (Secrets of Methamphetamine Manufacture, Fourth Edition, 1996)), the amount of free base denaturant a solvent extracts along with the sympathomimetic amine may be greater than 50% of the initial amount of denaturant; more preferably, the amount of denaturant extracted may be from about 60% to about 100% of the initial amount of denaturant; and most preferably, the amount of denaturant extracted may be from about 90% to about 100% of the initial amount of denaturant. The amount of denaturant extracted along with the sympathomimetic amine salts may be expected to vary depending on the particular extraction method employed.

Depending upon the extraction method employed, in general, the extent to which the denaturants effect the ease and efficiency of the recovery of sympathomimetic amine salts from sympathomimetic amine-containing formulations can be quantified. When the extraction method is that described by Uncle Fester in "The Secrets of Methamphetamine Manufacture", Fourth Edition, pages 158–159, after several hours the yield of sympathomimetic amine salt from the formulation is no more than about 70% of the total amount of sympathomimetic amine salt in the formulation. In a preferred embodiment of the present invention, the yield is no more than about 50%, and in a more preferred embodiment of the present invention, the yield is no more than about 30%, and in the most preferred embodiment, the yield is no more than about 10%.

Non-limiting examples of denaturants that may be used according to the invention are set forth below.

Amine Compounds

In a first series of non-limiting embodiments, acid salts of amine compounds that exist as substantially water soluble hydrophilic acid salts and substantially water insoluble hydrophobic free bases may be used as denaturants of the present invention. These amine compounds exhibit physical and chemical properties similar to sympathomimetic amine salts.

While preferred amine compound denaturants are discussed herein, it should be understood that any amine compound which exists as a substantially water soluble hydrophilic acid salt and a substantially water insoluble hydrophobic free base may be used as a denaturant. Such amine-containing denaturant compounds may have asymmetric centers and occur as racemates, racemic mixtures, individual diastereomers, or enatiomers, with all isomeric forms being included in the present invention.

In non-limiting embodiments of the present invention, the solubility of the amine compound denaturant and its free base is about the same as the solubility of the sympathomimetic amine salt and its free base, respectively. The denaturant and its free base will have similar solubility's in water and lipophilic solvent relative to sympathomimetic amines; the denaturant preferably being soluble in water and practically insoluble in a lipophilic solvent and its free base being sparingly soluble in water and freely soluble in a lipophilic solvent.

A preferred amine that meets the foregoing criteria is an acid addition salt of quinine (e.g., quinine monohydrochloride or quinine bisulfate). Quinine is very water soluble as a salt and is nearly insoluble in water as a free base. The free base, however, is quite soluble in a wide variety of organic solvents. Further, quinine has several functional groups which are reactive under the reduction conditions normally used to produce the illegal drug from pseudoephedrine hydrochloride or phenylpropanolamine hydrochloride. These additional side reactions make the general reaction mixture much more complicated and make it more difficult to purify the product. Quinine is also listed in the American "Generally Regarded as Safe" ("G.R.A.S.") list, and therefore may be considered to be pharmacologically and biologically acceptable to mammals.

In other non-limiting embodiments of the present invention, the amine compound denaturant is an acid salt of a compound having structural formula I:

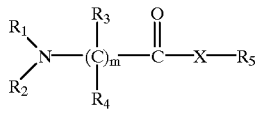

wherein $R_1$, $R_2$, $R_3$, $R_4$, and $R_5$ are selected from one of the following: hydrogen; substituted or unsubstituted $C_{1-12}$ alkyl; substituted or unsubstituted $C_{1-12}$ alkoxy; hydroxyl; halogen; substituted or unsubstituted aryl; and substituted or unsubstituted heterocycle. $R_3$ and $R_4$ may also be —$CH_2$—SY, where Y is hydrogen; substituted or unsubstituted $C_{1-12}$ alkyl; substituted or unsubstituted $C_{1-12}$ alkoxy; hydroxyl; halogen; substituted or unsubstituted aryl; and substituted or unsubstituted heterocycle. X may be oxygen, sulfur or nitrogen-$R_6$ wherein $R_6$ is the same as $R_1$. M is an integer from zero to five. Notwithstanding the foregoing, $R_1$ and $R_2$ cannot be halogen, $R_3$ and $R_4$ cannot be phenyl, and $R_5$ cannot be hydrogen or halogen. When any variable (e.g., aryl, heterocycle, $R_1$, $R_2$, $R_3$, etc), occurs more than one time in a constituent or in any formula of this invention, its definition on each occurrence is independent of its definition at every other occurrence. Also, combinations of substituents and/or variables are permissible only if such combinations result in stable compounds. As used herein except where noted, "alkyl" is intended to include both branched- and straight-chain saturated or unsaturated aliphatic hydrocarbon groups having the specified number of carbon atoms; "alkoxy" represents an alkyl group of indicated number of carbon atoms attached through an oxygen bridge. "Halogen" or "halo" as used herein, means fluoro-, chloro-, bromo-, and iodine or iodo-. As used herein, with exceptions as noted, "aryl" is intended to mean any stable monocyclic, bicyclic or tricyclic carbon ring having up to 7 members in each ring, wherein at least one ring is aromatic. The term heterocycle or heterocyclic, as used herein except where noted, represents a stable 5- to 7-membered monocyclic or stable 8-to 11-membered bicyclic heterocyclic ring which is either saturated or unsaturated, and which comprises carbon atoms and from one to three heteroatoms selected from the group consisting of nitrogen, oxygen and sulfur, wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

Preferred amine compound denaturants which are acid salts of compounds of structural formula I are salts of amino acid amides. Amino acid esters and amino acid amides are well known to those of skill in the art. Preferred examples of these denaturants include but are not limited to salts of cysteine ethyl ester, glycine t-butyl ester, leucinamide, methionine ethyl ester, methyl cysteine, methyl methionine, proline benzyl ester, serine ethyl ester, tryptophan methyl ester, and ethylglycine.

Additional denaturants suitable for the present invention include water soluble vitamins, including but not limited to vitamin B-1(thiamine hydrochloride), vitamin B-6 (pyridoxine hydrochloride) and salts of vitamin K5.

Odor-Producing Denaturants

In a second series of non-limiting embodiments, denaturants used according to the invention may be compounds which become odoriferous during purification and/or conversion of sympathomimetic amines in illegal drug synthesis. The odor is preferably unpleasant and pungent. The odor may be released during the preparation of illegal drugs, and thereby render such preparation distasteful and/or serve as a recognizable signal to law enforcement that illegal drugs are being prepared at a particular location. Illegal drugs prepared from starting materials that comprise odor-producing denaturant may themselves retain a distasteful odor and/or taste. However, such denaturants do not produce the unpleasant taste or odor when products comprising said denaturants are used in the legally intended manner.

In certain non-limiting embodiments of the invention, the odor-producing denaturant may contain sulfur, such that a sulfurous odor may be produced during purification/conversion. Examples of such sulfur-containing odor-producing denaturants include magnesium sulfate, sodium sulfate, the acid salts of sulfur-containing amino acids such as methionine HCl, ethyl cysteine HCl, ethyl methionine HCl, methyl cysteine HCl and methyl methionine HCl. When such sulfur-containing compounds are subjected to illegal reaction conditions, odoriferous hydrogen sulfide, low molecular weight mercaptans and/or sulfur dioxide will be produced.

In other non-limiting embodiments of the invention, the odor-producing denaturant may contain nitrogen. Examples of such nitrogen-containing odor-producing denaturants include ammonium chloride, ammonium sulfate, mono, di and trialkylamine hydrochlorides, succinamide and glutaric acid diamide. When such nitrogen-containing compounds are subjected to illegal reaction conditions, odoriferous ammonia, low molecular weight amines and low molecular weight diamines such as putrescine and cadaverine can be produced. The foregoing nitrogen-containing denaturants can develop their unpleasant odor during the alkaline extraction and isolation steps of the conversion process.

GUMS AND/OR VISCOSITY MODIFIERS

In a third series of non-limiting embodiments, denaturants used according to the invention may be compounds which are gums and/or viscosity modifiers. In a particular series of embodiments, the denaturant comprises one or more gum and viscosity modifier.

The gums and viscosity modifiers employed in the present invention are those which possess (i) good water solubility and/or swellability; and (ii) poor organic solvent solubility to prevent their preferential extraction. Gums and viscosity modifiers are known to those of skill in the art, but in a specific, non-limiting example, the material used is a polyethylene oxide compound which has very good water solubility and very poor lipophilic solvent solubility, and which forms a slimy, mucus-like gel in water. Polyethylene oxide compounds having a molecular weight of about 2,000,000 are particularly preferred (es, Polyox N-60K, Union Carbide). The molecular weight is measured by rheological methodology. Other non-limiting examples of gums and/or viscosity modifiers include xanthane gum, guar gum, and alkyl celluloses such as hydroxypropyl cellulose, hydroxypropylmethyl cellulose and hydroxyethyl cellulose.

In a particular series of embodiments, a combination of denaturants may be used which comprises one or more gum/viscosity modifier and one or more surfactant. While not intending to be bound by theory, the combination of the surfactant and the gum/viscosity modifier increases the rate of hydration of the gum/viscosity modifier and attempts to extract in organic solvents results in emulsification. Like the gum/viscosity modifier, the surfactant has very good water solubility and very poor lipophilic solvent solubility. Surfactants are known to those of skill in the art and may be non-ionic, cationic, anionic, soaps, precursors to soaps and amphoterics. In a specific, non-limiting example, the surfactant is (a) a poly(oxypropylene)poly(oxyethylene) copolymer which is a non-ionic surfactant/emulsifier/gelling agent with very good water solubility, and which forms a gel in water (eM, Pluronic F 127 which is an ethylene oxide, propylene oxide block copolymer corresponding to the formula $HO(C_2H_4O)_{101}(C_3H_6O)_{56}(C_2H_4O)_{101}H$ (BASF)), has poor solubility in lipophilic solvents at elevated levels of ethylene oxide substitution); and/or (b) sodium lauryl sulfate, an anionic surfactant/wetting agent with very good water solubility and very poor lipophilic solvent solubility, which accelerates both the rate as well as the extent of hydration of gum/viscosity modifier and some surfactants.

In a particular series of embodiments, a combination of denaturants may be used which comprises one or more gum/viscosity modifier, one or more surfactant, and one or more emulsifier, the combination of which is more difficult to separate, during purification procedures, from sympathomimetic amine, than any one of such denaturants used alone.

For example, a combination of two non-ionic surfactants/emulsifiers/thickeners and an ionic surfactant/emulsifier/wetting agent (each of which is separately considered a denaturant) may be used. In a specific, non-limiting example, the materials used in combination are (a) a polyethylene oxide compound; (b) a poly(oxypropylene)poly/oxyethylene)copolymer; and (c) sodium lauryl sulfate.

The amount of gums and/or viscosity modifiers added to the compositions of the present invention is that amount which is sufficient to have a denaturing effect. Depending on the formulation, the amount of gums and/or viscosity modifiers is that amount which is sufficient to have a denaturing effect on the composition, but ineffective to provide "controlled or sustained release" as these terms are generally understood to those skilled in the art. Stated another way, the amount of gums and/or viscosity modifiers is that amount which is sufficient to have a denaturing effect on the composition without compromising the immediate release nature of, or the bioavailability or dosing frequency associated with, over-the-counter sympathomimetic amine-containing compositions.

Such combinations of denaturants, which physically interfere with sympathomimetic amine purification, offer the following advantages. First, the difficulty of isolating sympathomimetic amine from products containing such denaturants is greatly increased. Moreover, the quantity of solvents and time needed to achieve adequate purification of sympathomimetic amines is increased. Further, the denaturant mixture decreases the yield of sympathomimetic amine produced per reaction. Each of the foregoing features tends to render illegal drug synthesis from products of the invention impractical due to poor efficiency, high cost, and augmented risk of discovery.

Encapsulated Gums and/or Viscosity Modifiers

In a fourth series of non-limiting embodiments, denaturants used according to the invention may be compounds which are encapsulated gums and/or viscosity modifiers. In a particular series of embodiments, the denaturant comprises more than one encapsulated gum and/or viscosity modifier.

While not intending to be bound by theory, the combination of the encapsulating material and the gum and/or viscosity modifier allows the presence of high amounts of gum and/or viscosity modifier in denaturant-containing formulations. As indicated in the previous section, gums and/or viscosity modifiers act as denaturants in sympathomimetic amine-containing formulations. Unfortunately, the presence of high amounts of gums and/or viscosity modifiers in the formulations can interfere with the dissolution of sympathornimetic amines from the formulations in their normal intended and regulated use. It is possible that over-the-counter medications containing high amounts of gums and/or viscosity modifiers will fail USP dissolution tests and raise regulatory concerns.

It has been discovered, however, that high amounts of gums and/or viscosity modifiers can be present in sympathomimetic amine-containing formulations if the denaturants are encapsulated in material that is either soluble in non-polar organics and insoluble in aqueous solutions or hydrophobic materials that have a moderately low melting temperature (i.e., between about 50° C. and about 90° C.). In short, the gums and/or viscosity modifiers would be free to act as denaturants when the sympathomimetic amine-containing formulations are misused in illegal operations, but would be relatively unavailable to interfere with dissolution and/or bioavailability when the formulations are used in their normal intended and regulated use. The concept can best be explained by the following non-limiting examples.

During many illegal operations, sympathomimetic amine-containing formulations are treated to a pre-soak in a non-polar organic like toluene which can remove any gums and/or viscosity modifiers in the formulations. It is proposed to encapsulate a denaturant like polyethylene oxide in a material that is soluble in toluene and insoluble in water. If the product is used in its normal intended and regulated use (i e., no exposure to non-polar organics in the human body) the denaturant will remain encapsulated and there is little or no interference with dissolution and/or bioavailability. If the product is misused (i.e., illegal drug operations), the toluene will extract the encapsulating material and release the polyethylene oxide to make purification of the sympathomimetic amine from the formulation extremely difficult.

In another example, it can be envisioned that illegal drug operators could minimize the denaturing effect of gums and/or viscosity modifiers by the use of increased temperatures. The filterability of materials from solution can often be improved by heating the solution to reduce the viscosity. If gums and/or viscosity modifiers are encapsulated in moderately low melting hydrophobic materials to minimize their interference with dissolution, and are added to a formulation already containing a denaturing amount of gum and/or viscosity modifier to make filtration of an aqueous solution unfeasable, it would eliminate the possibility of using the heating strategy to improve filterability. As the solution is heated, more gum and/or viscosity modifier would be released, compensating for any improvement in filterability as a result of the hotter solution. The concept would allow a higher level of gum and/or viscosity modifier to be added to the sympathomimetic amine-containing formulations without having any effect on the dissolution or bioavailability of the active drug. It would prevent or reduce the feasibility of circumventing the viscosity modifying denaturant system by using heat to improve the filterability of the aqueous drug-containing solution.

Such combinations of encapsulated denaturants, which physically interfere with sympathomimetic amine purification, offer the following advantages. First, the difficulty of isolating syrnpathomimetic amine from products containing such denaturants is greatly increased. Moreover, the quantity of solvents and time needed to achieve adequate purification of sympathomimetic amines is increased. Further, the denaturant mixture decreases the yield of sympathomimetic amine produced per reaction. Each of the foregoing features tends to render illegal drug synthesis from products of the invention impractical due to poor efficiency, high cost, and augmented risk of discovery.

The gums and viscosity modifiers employed in the present invention are those which possess (i) good water solubility and/or swellability; and (ii) poor organic solvent solubility to prevent their preferential extraction. Gums and viscosity modifiers are known to those of skill in the art, but in a specific, non-limiting example, the material used is a polyethylene oxide compound which has very good water solubility and very poor lipophilic solvent solubility, and which forms a slimy, mucus-like gel in water. Polyethylene oxide compounds having a molecular weight of about 2,000,000 are particularly preferred (e.g., Polyox N-60K, Union Carbide). Other non-limiting examples of gums and/or viscosity modifiers include xanthane gum, guar gum, and alkyl celluloses such as hydroxypropyl cellulose, hydroxypropylmethyl cellulose and hydroxyethyl cellulose.

In a particular series of embodiments, a combination of denaturants may be used which comprises one or more gum/viscosity modifier and one or more surfactant. While not intending to be bound by theory, the combination of the surfactant and the gum/viscosity modifier increases the rate of hydration of the gum/viscosity modifier and attempts to extract in organic solvents results in emulsification. Like the gum/viscosity modifier, the surfactant has very good water solubility and very poor lipophilic solvent solubility. Surfactants are known to those of skill in the art and may be non-ionic, cationic, anionic, soaps, precursors to soaps and amphoterics. In a specific, non-limiting example, the surfactant is (a) a poly(oxypropylene)poly(oxyethylene) copolymer which is a non-ionic surfactant/emulsifier/gelling agent with very good water solubility, and which forms a gel in water (es, Pluronic F 127 (BASF)), has poor solubility in lipophilic solvents at elevated levels of ethylene oxide substitution); and/or (b) sodium lauryl sulfate, an anionic surfactant/wetting agent with very good water solubility and very poor lipophilic solvent solubility, which accelerates both the rate as well as the extent of hydration of gum/viscosity modifier and some surfactants.

In a particular series of embodiments, a combination of denaturants may be used which comprises one or more gum/viscosity modifier, one or more surfactant, and one or more emulsifier, the combination of which is more difficult to separate, during purification procedures, from sympathomimetic amine, than any one of such denaturants used alone.

For example, a combination of two non-ionic surfactants/emulsifiers/thickeners and an ionic surfactant/emulsifier/wetting agent (each of which is separately considered a denaturant) may be used. In a specific, non-limiting example, the materials used in combination are (a) a polyethylene oxide compound; (b) a poly(oxypropylene)poly/oxyethylene)copolymer, and (c) sodium lauryl sulfate.

The encapsulating material employed in the present invention is one which is very soluble in non-polar organics, such as toluene and insoluble in water and/or a hydrophobic material that is low-melting (i.e., between about 50° C. and about 90° C.). Encapsulating materials are known to those of skill in the art, but in a specific, non-limiting example, the encapsulating material used include fatty acids, natural waxes, synthetic waxes, and the like, and mixtures thereof.

Fatty acids are generally defined in the following section. Particularly preferred fatty acids include hydrogenated palm oil, hydrogenated castor oil, hydrogenated cottonseed oil, stearic acid, palmitic acid, and mixtures thereof.

Waxes are low melting organic mixtures or compounds having a high molecular weight, are solid at room temperature and generally are similar in composition to fats and oils except that waxes contain no glycerides. Waxes may be hydrocarbons or esters of fatty acids and alcohols. Waxes useful in the present invention include natural waxes, such as animal waxes, vegetable waxes, and petroleum waxes (i.e., paraffin wax, spermaceti wax, carnauba wax, Japan wax, baberry wax, flax wax, beeswax, Chinese wax, shellac wax, lanolin wax, sugarcane wax, candelilla wax, microcrystalline wax, petrolatum wax, carbowax, and the like, and mixtures thereof).

The amount of encapsulating material used to encapsulate the gum and/or viscosity modifier is that amount which is effective to resist or prevent the release of the gum and/or viscosity modifier during normal human digestion of the denaturant-containing formulations, yet allows the removal of the gum and/or viscosity modifier from the formulations during misuse (i.e., a non-polar pre-soak phase of the normal clandestine procedure to produce illegal drugs from sympathomimetic amines or through increased temperatures to circumvent a viscosity modifying denaturant system). In one embodiment, the encapsulating material should be a material that can coat the gum and/or viscosity modifier and be extracted in substantial amounts from the gum and/or viscosity modifier in a formulation by a non-polar organic, i e., for about 30 to about 40 minutes in a toluene pre-soak.

Encapsulated Solvent Soluble Soap Precursors/Surfactants

In a fifth series of non-limiting embodiments, denaturants used according to the invention may be compounds which are encapsulated soap precursors and/or surfactants that are soluble in non-polar organic solvents, including but not limited to encapsulated fatty acids. In a particular series of embodiments, the denaturant comprises more than one encapsulated solvent soluble soap precursor/surfactant.

While not intending to be bound by theory, the combination of the encapsulating material and the solvent soluble soap precursor and/or surfactant prevents or resists the extraction of the soap precursor and/or surfactant from sympathomimetic amnine-containing formulations if the formulations are treated to a pre-soak of a non-polar organic like toluene during the normal clandestine procedure to produce illegal drugs from sympathomimetic amine-containing formulations. Soap precursors and surfactants themselves act as denaturants, but are susceptible to extraction by a pre-soak of a non-polar organic. If the soap precursors and surfactants are encapsulated in a material that is poorly soluble in non-polar solvents, but soluble in water, they will remain in the sympathomimetic amine--containing formulations during the solvent wash. Later if the formulations are slurried in water the encapsulated material is dissolved and the soap precursors and/or surfactants are released to physically interfere with the sympathomimetic amine purification.

In a preferred, non-limiting example of the present invention, fatty acids are soap precursors that are soluble in non-polar organics like toluene. Fatty acids are carboxylic acids derived from or contained in an animal or vegetable fat or oil. Fatty acids are composed of a chain of alkyl groups containing from 4 to 22 carbon atoms and are characterized by a terminal carboxyl group.

Fatty acids useful in the present invention are selected from the group consisting of decenoic acid, docosanoic acid, stearic acid, palmitic acid, lauric acid, myristic acid, oleic acid, and the like, and mixtures thereof. The preferred fatty acids are selected from the group consisting of stearic acid, paimitic acid, oleic acid, and mixtures thereof. The most preferred fatty acid is stearic acid.

In a preferred, non-limiting example of the present invention, esters of fatty acids or fatty alcohols act as surfactants that are soluble in non-polar organics like toluene. Esters of a fatty acid having from about 10 to about 31 carbon atoms and fatty alcohols having from about 12 to about 31 carbon atoms, the ester having a carbon atom content from about 24 to about 62 carbon atoms, are particularly preferred.

Examples of fatty acid esters include monglyceryl ester, diglyceryl ester, or triglyceryl ester (glycerides) which is an ester formed from a fatty acid having from about 10 to about 3 1 carbon atoms and glycerol, wherein one or more of the hydroxyl groups of glycerol is substituted by a fatty acid. Examples of useful glycerides include glyceryl monostrearate, glyceryl distearate, glyceryl tristearate, glyceryl dipaimitate, glyceryl tripalmitate, glyceryl monopalmitate, glyceryl dilaurate, glyceryl trilaurate, glyceryl monolaurage, glyceryl didocosanoate, glyceryl tridocosanoate, glyceryl monodocosancate, glyceryl monocaproate, glyceryl dicaproate, glyceryl tricaproate, glyceryl monomyristate, glyceryl dimyristate, glyceryl trimyristate, glyceryl monodcenoate, glyceryl didecenoate, glyceryl tridecenoate, and the like, and mixtures thereof. The preferred glycerides are selected from the group consisting of glyceryl monostearate, glyceryl distearate, glyceryl tristearate, and mixture thereof.

In a preferred embodiment, the solvent soluble soap precursor and/or surfactant is selected from the group consisting of stearic acid, glycerol monooleate and glycerol monostearate. More preferably, the solvent soluble soap precursor and/or surfactant is stearic acid.

The encapsulating material employed in the present invention is one which is poorly soluble in non-polar organics, such as toluene and soluble in water. Encapsulating materials are known to those of skill in the art, but in a specific, non-limiting example, the encapsulating material used is maltodextrin, dextrin, acacia, and alkyl celluloses such as hydroxeypropylmethyl cellulose, hydroxypropyl cellulose and hydroxyethyl cellulose.

The amount of encapsulating material used to encapsulate the solvent soluble soap precursors andlor surfactants is that amount which is effective to resist or prevent the removal of the soap precursors and surfactants from the formulations during a non-polar pre-soak phase of the normal clandestine procedure to produce illegal drugs from sympathornimetic amines. In general, the encapsulating material should be a material that can coat the soap precursors and surfactants, and prevent the extraction of a substantial amount of the soap precursors and surfactants from a formulation by a non-polar organic, i.e., for about 30 to about 40 minutes in a toluene pre-soak.

The encapsulated denaturants, which physically interfere with sympathomimetic amine purification, offer the following advantages. First, the difficulty of isolating sympathomimetic amine from products containing such denaturants is greatly increased. Moreover, the quantity of solvents and time needed to achieve adequate purification of sympathomimetic amines is increased. Further, the denaturant mixture decreases the yield of sympathomimetic amine produced per reaction. Each of the foregoing factors tends to render illegal drug synthesis from products of the invention impractical due to poor efficiency, high cost, and augmented risk of discovery.

Sympathomimetic Amines

Sympathomimetic amines are those compounds which cause vasoconstriction in the vascular bed of the nasal mucosa which results in a shrinking of the engorged mucous membranes and thus promote drainage and improve nasal air flow. In a preferred embodiment of the present invention, the sympathomimetic amines of the present invention are those with structural formula II:

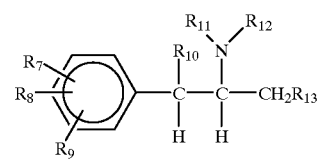

wherein $R_7$, $R_8$, $R_9$, $R_{10}$, $R_{11}$, $R_{12}$ and $R_{13}$ are selected from the following: hydrogen; substituted or unsubstituted $Cl_{1-12}$ alkyl; substituted or unsubstituted $C_{1-12}$ alkoxy; hydroxy; and halogen. Notwithstanding the foregoing, $R_{11}$ and $R_{12}$ are not halogens. As used herein, the term "sympathomimetic amine" may refer to a phamaceutically acceptable acid addition salt of a compound which may have asynunetric centers and occur as racemates, racemic mixtures, individual diastereomers, or enantiomers, with all isomeric forms being included in the present invention.

In a particularly preferred embodiment of the present invention, the sympathomimetic amines are used commercially as nasal decongestants. Specific examples of acid salts of sympathomimetic amine decongestants commonly found in OTC medications include: phenylephrine hydrochloride, phenylpropanolamine hydrochloride, pseudoephedrine hydrochloride, pseudoephedrine sulfate and ephedrine hydrochloride.

Examples of illegal drugs which are converted from sympathomimetic amines include, but are not limited to, methamphetamine, amphetamine, methcathinone, and cathinone. The conversion of illegal drugs from sympathorimetic amine-containing amines is known to those of skill in the art and occurs through a variety of oxidative or reductive reactions.

Compositions

The amount of denaturant(s) and sympathomimetic amine salts in any composition of the present invention is in a ratio from about 100:1 to about 1:100, preferably from about 10:1 to about 1:10. More preferably, the amount of denaturant(s) and sympathomimetic amine salts in any composition of the present invention is in a ratio from about 3:1 to about 1:3. Most preferably, the amount of denaturant(s) and sympathomimetic amine salts in any composition of the present invention is in a ratio from about 2:1 to about 1:2.

Generally the total quantity of denaturant(s) in a unit dose preparation may be varied or adjusted from about 0.1 mg to about 750 mg according to the particular application and the potency of the sympathomimetic amine salt. When pseudoephedrine hydrochloride is the sympathomimetic amine salt, the concentration of the denaturant(s) is in a range from about 0.3 mg to about 300 mg; most preferably, in a range from about 10 mg to about 90 mg; and most preferably, in a range from about 15 mg to about 60 mg. When phenylpropanolamine hydrochloride is the sympathomimetic amine salt, the concentration of the denaturant(s) is in the range from about 7.5 mg to about 750 mg; more preferably, in the range from about 25 mg to about 225 mg; most preferably, in the range from about 37.5 mg to about 75mg.

The present invention is also directed to methods of preparing the denaturant/sympathomimetic amine salt combinations. The combinations are prepared by adding an effective amount of at least one denaturant to a sympathomimetic amine salt-containing pharmaceutical composition. The denaturant(s) may be added individually or as a mixture to the pharmaceutical composition. The present invention is also directed to products made by such methods of preparation.

Pharmaceutical compositions comprising the denaturant(s) and the sympathomimetic amine salt(s) (and when desired other pharmaceutical actives in an intimate admixture with a pharmaceutical carrier) may be prepared according to conventional pharmaceutical compounding techniques. The compositions may take a wide variety of forms depending on the form of preparation desired for administration, e.g., intravenous, oral or parenteral. The compositions according to this invention may, for example, take the form of tablets, capsules, granules, powders, or lozenges, or liquid preparations such as solutions and non-aqueous suspensions.

The compositions may be formulated using conventional carriers or excipients and well established techniques. Without being limited thereto, such conventional carriers or excipients include diluents, binders and adhesives (e.g., cellulose derivatives and acrylic derivatives), lubricants (e.g., magnesium or calcium stearate, or vegetable oils, polyethylene glycols, talc, sodium lauryl sulphate, polyoxyl ethylene monostearate), disintegrants, colorants, flavorings, preservatives, sweeteners and miscellaneous materials such as buffers and adsorbents (some of which would be considered denaturants) in order to prepare a particular composition.

Non-aqueous suspensions may be obtained by dispersing the denaturant/sympathomimetic amine compositions in a suitable non-aqueous based vehicle, optionally with the addition of suitable viscosity enhancing agent(s) (e.g., hydrogenated edible fats, aluminum stearate, etc.). Suitable non-aqueous vehicles include, for example, almond oil, arachis oil, soybean oil or fractionated vegetable oils such as fractionated coconut oil. Preservative(s) (e.g., methyl, ethyl, propyl or butyl-hydroxybenzoates, sodium benzoate or sorbic acid, etc.) may be included as appropriate.

A wide variety of medicaments may further be present in the denaturant/sympathomimetic amine combinations of the present invention. The medicament drugs may be selected from a wide variety of drugs and their acid addition salts. Suitable categories of drugs that may be employed may vary widely. Illustrative categories and specific examples include a) antitussives, such as dextromethorphan, dextromethorphan hydrobromide, noscapine, carbetapentane citrate, and chiophedianol hydrochloride; b) antihistamines, such as chlorpheniramine maleate, phenindamine tartrate, pyrilamine maleate, doxylamine succinate, phenyltoloxamine citrate, diphenhydramine hydrochloride, promethazine and triprolidine; c) antiasthmatic drugs, J2-adrenergics, e.g. salbutamol (albuterol), terbutaline, carbuterol, broxaterol, aminophylline, theophylline; d) analgesics such as acetaminophen; and e) non-steroidal antiinflammatory drugs (NSAID), such as acetylsalicylic acid, indomethacin, acemethacin, sulindac, piroxicam, ibuprofen, naproxen, ketoprofen.

Any combinations, compositions or products described herein are used for known indications treated by sympathomimetic amines.

The following non-limiting examples illustrate the inventor's preferred methods for preparing the denatured-sympathorimetic amine salt compositions of the invention.

EXAMPLES

Example 1

Pharmaceutical tablets were prepared according to well known formulation procedures. The tablets contained pseudoephedrine hydrochloride and quinine hydrochloride in ratios of 30:25 and 30:12.5.

| Sample A MATERIAL | MG/DOSE | Number of doses: 250 /BATCH | % (W/W) |
|---|---|---|---|
| 1. Pseudoephedrine HCl | 30.00 | 7.50 | 18.297% |
| 2. Quinine HCl | 25.00 | 6.25 | 15.2439% |
| 3. Povidone (K29–32) | 2.00 | 0.50 | 1.2195% |
| 4. Microcrystalline cellulose PH102 | 50.00 | 12.50 | 30.4878% |
| 5. Corn Starch | 5.00 | 1.25 | 3.0488% |
| 6. Lactose, Fast Flo | 50.00 | 12.50 | 30.4878% |
| 7. Stearic acid | 1.60 | 0.40 | 0.9756% |
| 8. Magnesium stearate | 0.40 | 0.10 | 0.2439% |
| Totals | 164.00 | 41.00 | 100.0000% |

A. Combined materials 1–6.
B. Added material 7 and 8 to a small portion of the batch and blended (lube blend).
C. Added lube blend to the batch and blended well.

| Sample B MATERIAL | MG/DOSE | Number of doses: 250 G/BATCH | % (W/W) |
|---|---|---|---|
| 1. Pseudoephedrine HCl | 30.00 | 7.50 | 18.297% |
| 2. Quinine HCl | 12.50 | 3.13 | 7.6200% |
| 3. Povidone (K29–32) | 2.00 | 0.50 | 1.2195% |
| 4. Microcrystalline cellulose PH102 | 56.25 | 14.06 | 34.2988% |
| 5. Corn Starch | 5.00 | 1.25 | 3.0488% |
| 6. Lactose, Fast Flo | 56.25 | 14.06 | 34.2988% |
| 7. Stearic acid | 1.60 | 0.40 | 0.9756% |
| 8. Magnesium stearate | 0.40 | 0.10 | 0.2439% |
| Totals | 164.00 | 41.00 | 100,0000% |

A. Combined materials 1–6.
B. Added material 7 and 8 to a small portion of the batch and blended (lube blend).
C. Added lube blend to the batch and blended well.

Example 2

An extraction study was completed to determine the separatability of pseudoephedrine hydrochloride and quinine hydrochloride from tablets prepared according to Example 1. The study was conducted to evaluate the suitability of using quinine hydrochloride as a denaturant for pseudoephedrine hydrochloride. It was concluded from the study that isolation of pure pseudoephedrine hydrochloride from a quinine hydrochloride/pseudoephedrine hydrochloride combination product cannot be accomplished using conventional extraction techniques with organic solvents like ether.

Experiment

Two lots of Example 1 tablets containing pseudoephedrine hydrochloride and quinine hydrochloride in ratios 30:25 and 30:12.5 were submitted for determining the separability of the two components from each other.

The following extraction procedure was carried out for each lot of the tablets.

The sample was first dissolved in water and the insoluble excipients were allowed to settle. The pseudoephedrine hydrochloride and quinine hydrochloride content in this solution was determined by HPLC. An aliquot of the supernatant liquid was then transferred to a separating funnel, sodium hydroxide solution was added and the solution was shaken. A precipitate was formed and the solution became cloudy indicating formation of pseudoephedrine free base. As a purification step two extractions with ethyl ether were made to extract pseudoephedrine free base and quinine into the ether phase. Finally an aliquot of the ether phase was extracted with two portions of 1.0 N hydrochloride to reform the hydrochloride salts. The hydrochloride extracts were then tested by HPLC to determine the relative efficiency of the extraction process. A peak purity determination of pseudoephedrine hydrochloride and quinine hydrochloride peak in the chromatograms of before and after extraction samples showed the peaks to be pure.

|   | Pseudoephedrine-HCl (% LC) | | | Quinine-hyrdrochloride (% LC) | | |
|---|---|---|---|---|---|---|
|   | Starting Solution | Final Solution | Percent Recovery | Starting Solution | Final Solution | Percent Recovery |
| A | 98.9 | 98.8 | 99.9 | 95.8 | 96.7 | 100.0 |
| B | 97.6 | 97.8 | 100.2 | 92.6 | 93.2 | 100.6 |

Quinine-hydrochloride was measured as a mixture of quinine hydrochloride and dihydroquinine hydrochloride. The percentage of dihydroquinine in quinine hydrochloride was found to be <5% by area percent.

Example 3

This a formulation for tablets denatured by a gum/surfactant system which are then sugar coated.

| # | Material | mg/dose | # of doses g/batch | 140,000 % (w/w) Core |
|---|---|---|---|---|
| 1 | Pluronic F127 | 5.00 | 700.00 | 6.9444% |
| 2 | Polyox N-60K | 2.00 | 280.00 | 2.7778% |
| 3 | Sodium lauryl sulfate washed and dried | 0.50 | 70.00 | 0.6944% |
| 4 | Pseudoephedrine HCl | 30.00 | 4200.00 | 41.6667% |
| 5 | Lactose | 27.30 | 3822.00 | 37.9167% |
| 6 | Cornstarch | 2.00 | 280.00 | 2.7778% |
| 7 | Stearic acid | 5.00 | 700.00 | 6.9444% |
| 8 | Magnesium stearate | 0.20 | 28.00 | 0.2778% |
|   | Total wt for core | 72.00 | 10080.00 | 100.0000% |

Process:
A. Combined 1–6 in a PK mixer.
B. Blended 15 minutes
C. Withdrew 2 kg of the powder blend from the mixer.
D. Combined 7 and 8 W/approx. 2 Kg of C.
E. Blended for 5 minutes.

Example 4

This is a formulation for tablets denatured by a gum/surfactant system.

| # | Material | mg/dose | # of doses g/batch | 15,000 % (w/w) |
|---|---|---|---|---|
| 1 | Pseudoephedrine HCl | 60.00 | 900.00 | 23.0769% |
| 2 | Pluronic FI27 | 5.00 | 75.00 | 1.9231% |
| 3 | Polyox | 2.00 | 30.00 | 0.7692% |

-continued

| # | Material | mg/dose | # of doses g/batch | 15,000 % (w/w) |
|---|---|---|---|---|
| 4 | Sodium lauryl sulfate washed and dried | 0.50 | 7.50 | 0.1923% |
| 5 | Emcompress | 75.5 | 1132.50 | 29.0385% |
| 6 | Triprolidine HCl adsorbate | 20.00 | 300.00 | 7.6923% |
| 7 | Cab-O-Sil M-5 (SiO2) | 0.50 | 7.50 | 0.1923% |
| 8 | Avicel PH102 | 45.00 | 675.00 | 17.3077% |
| 9 | Crospovidone | 8.00 | 120.00 | 3.0769% |
| 10 | Starch 1500 | 27.00 | 405.00 | 10.3846% |
| 11 | Stearic acid | 16.00 | 240.00 | 6.1538% |
| 12 | Magnesium stearate | 0.50 | 7.50 | 0.1923% |
|   | Total wt for core | 260.00 | 3,900.00 | 100.0000% |
| 13 | Opadry YS-1-7059 | 7.80 | 117.00 | 3.0000%** |
| 14 | Candelilla wax | 0.10 | 1.50 | 0.0385%** |

** % of core tablet weight

Process:
A Blended materials 1–11 in a P-K blender for 15 minutes.
B Added material 12 to approximately 200 g of blended A.
C Added C to the blended material and blended for 5 minutes.
D Material #13 prepared as a 10% solution in DI water.
E Core tablets spray coated with D.
F Coated tablets polished w/#14.

Example 5

This a formulation for core tablets denatured by a gumi-surfactant systems.

| # | Material | mg/dose | # of doses g/batch | 3000 % (w/w) |
|---|---|---|---|---|
| 1 | Pluronic F127 | 5.00 | 15.00 | 5.4348% |
| 2 | Polyox N-60K | 1.80 | 5.40 | 1.9565% |
| 3 | Sodium lauryl sulfate washed and dried | 0.50 | 1.50 | 0.5435% |
| 4 | Pseudoephedrine sulfate | 30.00 | 90.00 | 32.6087% |
| 5 | Methyl methionine HCl | 3.00 | 9.00 | 3.2609% |
| 6 | Avicel PH102 | 2.00 | 6.00 | 2.1739% |
| 7 | Lactose | 30.00 | 90.00 | 32.6087% |
| 8 | Cornstarch | 5.80 | 17.40 | 6.3043% |
| 9 | Titanium dioxide USP | 0.50 | 1.50 | 0.5435% |
| 10 | Cab-O-Sil M-5 (SiO2) | 0.20 | 0.60 | 0.2174% |
| 11 | Starch 1500 | 2.70 | 8.10 | 2.9348% |
| 12 | Stearic acid | 10.00 | 30.00 | 10.8696% |
| 13 | Magnesium stearate | 0.50 | 1.50 | 0.5435% |
| Total wt for core | | 92.00 | 276.00 | 100.0000% |

Process:
A Combined 1, 2, 3, 6, 9, 10 and 11. Blended, Screen 30 mesh.
B Combined 5 and 8. Blended.
C To C added 4, blended, added 7, blended. Screen 30 mesh.
D Added B to C.
E Screen 30 mesh.
F Combined 12 and 13. Screen 30 mesh.
G Added F to batch and blended. Tablet weight 92 mg/tablet.

Example 6

This is a formulation for core tablets denatured by a methylmethionine HCl.

| # | Material | mg/dose | # of doses g/batch | 10,000 % (w/w) Core |
|---|---|---|---|---|
| 1 | Pseudoephedrine sulfate | 30.00 | 300.00 | 37.5000% |
| 2 | Methyl methionine HCl | 3.00 | 30.00 | 3.7500% |
| 3 | Avicel PH102 | 2.00 | 20.00 | 2.5000% |
| 4 | Lactose | 26.50 | 265.00 | 33.1250% |
| 5 | Corn starch | 5.80 | 58.00 | 7.2500% |
| 6 | Cab-O-Sil M-5 (SiO$_2$) | 0.20 | 2.00 | 0.2500% |
| 7 | Starch 1500 | 2.00 | 20.00 | 2.5000% |
| 8 | Stearic acid | 10.00 | 100.00 | 12.5000% |
| 9 | Magnesium stearate | 0.50 | 5.00 | 0.6250% |
| | Total wt for core | 80.00 | 800.00 | 100.0000% |

A Blended materials 1–8 in a P-K blender for 15 minutes.
B Added materials 9 to approximately 100 g of blended A.
C Added B to the blended material and blended for 5 minutes.
Tablet weight 92 mg/tablet Example 7

This is a formulation for core tablets denatured by methylmethionine HCl.

| # | Material | mg/dose | # of doses g/batch | 10,000 % (w/w) |
|---|---|---|---|---|
| 1 | Polyox N-60K | 2.00 | 20.00 | 2.3529% |
| 2 | Pseudoephedrine sulfate | 30.00 | 300.00 | 35.2941% |
| 3 | Methyl methionine HCl | 3.00 | 30.00 | 3.5294% |
| 4 | Avicel PH102 | 2.00 | 20.00 | 2.3529% |
| 5 | Lactose | 28.80 | 288.00 | 33.8824% |
| 6 | Corn starch | 5.80 | 58.00 | 6.8235% |
| 7 | Cab-O-Sil M-5 (SiO$_2$) | 0.20 | 2.00 | 0.2353% |
| 8 | Starch 1500 | 2.70 | 27.00 | 3.1765% |
| 9 | Stearic acid | 10.00 | 100.00 | 11.7647% |
| 10 | Magnesium stearate | 0.50 | 5.00 | 0.5882% |
| | Total wt for core | 85.00 | 850.00 | 100.0000% |

Process:

A Blended materials 1–9 in a P-K blender for 15 minutes.
B Added materials 10 to approximately 100 g of blended A.
C Added B to the blended material and blended for 5 minutes.

Example 8

Purpose: Produce Encapsulated Polyethylene Oxide

| # | Material | mg/dose | # of doses g/batch | 1000 % (w/w) |
|---|---|---|---|---|
| 1 | Candelilla wax | 15.00 | 15.00 | 75.0000% |
| 2 | Polyethylene oxide | 5.00 | 5.00 | 25.0000% |
| | Core weight | 20.00 | 20.00 | 100.0000% |

Melt #1, Add #2, and cool to room temperature. Mill to a particle size compatible with the other materials in the final formulation.

Example 9

Purpose: Produce Encapsulated Xanthan Gum

| # | Material | mg/dose | # of doses g/batch | 1000 % (w/w) |
|---|---|---|---|---|
| 1 | Carnauba wax | 15.00 | 15.00 | 85.7143% |
| 2 | Xanthane gum | 2.50 | 2.50 | 14.2857% |
| | Core weight | 17.50 | 17.50 | 100.0000% |

Melt #1, Add #2, and cool to room temperature. Mill to a particle size compatible with the other materials in the final formulation.

Example 10

Purpose: Produce Encapsulated Hydroxypropylmethyl Cellulose

| # | Material | mg/dose | # of doses g/batch | 1000 % (w/w) |
|---|---|---|---|---|
| 1 | Stearic acid | 20.00 | 20.00 | 80.0000% |
| 2 | Hydroxypropylmethyl cellulose | 5.0 | 5.00 | 20.0000% |
| | Core weight | 17.50 | 17.50 | 100.0000% |

Melt #1, Add #2, and cool to room temperature. Mill to a particle size compatible with the other materials in the final formulation.

Example 11

Purpose: Produce Encapsulated Guar Gum

| # | Material | mg/dose | # of doses g/batch | 1000 % (w/w) |
|---|---|---|---|---|
| 1 | Paraffin wax | 12.50 | 12.50 | 83.3333% |
| 2 | Guar gum | 2.50 | 2.50 | 16.6667% |
| | Core weight | 15.00 | 15.00 | 100.0000% |

Melt #1, Add #2, and cool to room temperature. Mill to a particle size compatible with the other materials in the final formulation.

Example 12

Purpose: Produce Encapsulated Hydroxyethyl Cellulose

| # | Material | mg/dose | # of doses g/batch | 1000 % (w/w) |
|---|---|---|---|---|
| 1 | Carnauba wax | 15.00 | 15.00 | 66.6667% |
| 2 | Candelilla wax | 5.00 | 5.00 | 22.2222% |
| 3 | Hydroxyethyl cellulose | 2.50 | 2.50 | 11.1111% |
| | Core weight | 22.50 | 22.50 | 100.0000% |

Melt #1, Add #2, and cool to room temperature. Mill to a particle size compatible with the other materials in the final formulation.

Example 13

Using the procedure reported by Uncle Fester in "*The Secrets of Methamphetamine Manufacture*", extractions of various pseudoephedrine HCl containing products were conducted. Extracted were SUDAFED tablets, SUDAFED tablets w/denaturant, a blend of generic PSE tablets, and the same blend of PSE tablets w/denaturants. The denaturant system used was composed of 2 mg polyethylene oxide (Polyox), 5 mg of poloxamer (Carbopol), and 0.5 mg sodium lauryl sulfate (SLS).

| | | | |
|---|---|---|---|
| SUDAFED tablets | A | 89% | |
| SUDAFED w/denaturant | B | 0% | (recovery not practicable) |
| Generic tablets | E | 98% | |
| Generic w/denaturants | F | 0% | (recovery not practicable) |

SUMMARY

A series of extraction experiments was conducted to determine the extent to which the denaturant system effected the ease and efficiency of the recovery of pseudoephedrine (PSE) from finished products. Using the process described by Uncle Fester in "The Secrets of Methamphetamine Manufacture", Fourth Edition, page 158–9, five products, each containing 30 mg of pseudoephedrine HCl (PSE-HCl) per tablet, were evaluated. The products were:

SUDAFED 30 mg Tablets

SUDAFED 30 mg Tablets w/denaturant

Generic 30 mg Tablets

Generic 30 mg Tablets w/denaturant (added to the ground tablets)

It was not possible to filter the two products containing the denaturant system. Using the "Uncle Fester" process, no PSE was recovered from the denatured products. It may be possible to isolate the PSE from these formulations, but it would require considerable time, effort and expertise. Quantities of PSE were extractable from the three products without the denaturant system. The material was approximately 95% pure without further purification. The two products with PSE-HCl as the only active gave nearly complete recovery. The SUDAFED 30 mg Tablets produced 89% as pure PSE and the Generic 30 mg Tablets yielded 98% as pure PSE.

The denaturant system was effective in preventing the isolation of PSE from the tablets.

Materials

The Generic 30 mg Tablets w/denaturant were the ground Generic 30 mg Tablets to which the denaturant mixture was added during the initial toluene extraction.

| Exp | Product | Lot # | Supplier | Exp. Date |
|---|---|---|---|---|
| A | SUDAFED 30 mg Tablet | | | |
| B | SUDAFED 30 mg Tablet w/denaturant | | | |
| E | Generic 30 mg Tablets | (10%) 6HA095 | CVS Pharm. | 6/98 |
| | | (40%) 6KA008 | K-Mart | 9/98 |
| | | (50%) 5GO2096 | Walgreen Co. | 9/97 |
| F | Generic 30 mg Tablets | (10%) 6HA095 | CVS Pharm. | 6/98 |
| | | (40%) 6KA008 | K-Mart | 9/98 |
| | | (50%) 5GO2096 | Walgreen Co. | 9/97 |

The toluene was reagent grade. The sodium hydroxide 20% solution was prepared with deionized water and sodium hydroxide NF. All water was deionized.

Equipment

All extractions were stirred using magnetic stirring bars. Vacuum filtrations were conducted using the "house vacuum" at 22–25 mm of Hg. The filtrations were conducted with either Whatman #1 filter paper or Mr. Coffee coffee filters. The vacuum filter funnels were either 7.5 cm or 11 cm diameter Coors porcelain funnels.

The liquid/liquid toluene extractions were accomplished with a 500 ml separatory funnel and the toluene was evaporated on a Buchi 011 Rotavapor using "house vacuum" and an 800C. water bath.

Procedure:

1. The tablets are ground in a mortar and screened through a 20 mesh screen.
2. The ground tablets are slurried in 300 ml of toluene and stirred for one (1) hour. This step is conducted to try and remove the gum denaturant system.
3. The slurry is vacuum filtered. The filter cake washed with an additional 100 ml toluene and air died. The toluene solution is discarded.
4. The filter cake is added to 175 ml of room temperature. water, stirred for 1 hour and then vacuum filtered.
5. The filter cake is washed with an additional 50 ml of water. The filtrates are combined.
6. The combined filtrate is neutralized with 20% NaOH solution to a pH>12 and stirred for one (1) hour.
7. The batch is vacuum filtered to remove precipitated pseudoephedrine free base. The solid free base is washed with 50 ml of water and air dried. The filtrates and the wash are combined and extracted with 2×100 ml volumes of toluene. The toluene is evaporated to dryness and the resultant free base added to that obtained by filtration.
8. The theoretical yield is 12.29 g pseudoephedrine free base.

Results

A: Sudafed 30 MG Tablets

The toluene extraction of the ground tablets filtered very quickly (<30 seconds). The aqueous slurry of the ground tablets was only slightly viscous, probably due to the sugar, and it filtered without difficulty. After rinsing, the filter cake was very light pink and the filtrate a deep red. Upon the addition of sodium hydroxide, a significant quantity of flocculant material formed. This solid material, the pseudoephedrine free base, was easily collected by vacuum filtration and air dried. The solid had a light pink coloration. 10.56 g of solids were recovered. Toluene extraction followed by evaporation led to an additional 0.9 g of solid. Total yield is 11.468 g of crude material. Analytical Chemistry analysis shows the material to be 96.3% PSE. Actual yield of PSE is 11.04 g of PSE or 90% of theory.

B: Sudafed 30 MG Tablets W/Denaturant

The toluene extraction of the ground tablets filtered very quickly (<30 seconds). The aqueous slurry of the ground tablets was viscous, and very slimy. This was due to both the sugar and the Polyox. There was no significant sedimentation even after standing for 24 hours. The slurry was not filterable in either the 7.5 cm funnel with #1 paper or the 11 cm funnel with the Mr. Coffee filters After the slurry was first placed in the funnel, a small amount of water passed through. Within 10 minutes, the flow rate was down to less than one drop per 15 seconds and slowing. Neither filter produced more than 20 ml of filtrate before slowing to a near stop. The filtration and thus ready isolation of the free base is not feasible from this formulation.

E: Generic 30 MG Tablets

The toluene extraction of the ground tablets filtered very quickly (<30 seconds). The aqueous slurry of the ground tablets filtered without difficulty. After rinsing, the filter cake was very light pink and the filtrate a deep red. Upon the addition of sodium hydroxide, a significant quantity of flocculant material formed. This solid material, the free base, was easily collected by vacuum filtration and air dried. The solid had a light pink coloration. 10.04 g of solids were recovered. Toluene extraction followed by evaporation lead to an additional 02.7 g of solid. Total yield is 12.74 g of crude material. Analytical Chemistry analysis shows the material to be 94.75% PSE. Actual yield of PSE is 12.07 g of PSE or 98% of theory.

F: Generic 30 MG Tablets W/Denaturant

The toluene extraction of the ground tablets filtered very quickly (<30 seconds). The aqueous slurry of the ground tablets was viscous, and very slimy. This was due to the Polyox. There was slight sedimentation after standing for 24 hours. The settled material appeared to be dicalcium phosphate. The slurry was not filterable in either the 7.5 cm funnel with #1 paper or the 11 cm funnel with the Mr. Coffee filters After the slurry was first placed in the finnel, a small amount of water passed through. Within 10 minutes, the flow rate was down to less than one drop per 15 seconds and slowing. Neither filter produced more than 20 ml of filtrate before slowing to a near stop. The filtration and thus ready isolation of the free base is not feasible from this formulation.

| Exp | Product Crude | Yield Purity (%) | Yield PSE | % Yield |
|---|---|---|---|---|
| A SUDAFED 30 mg Tablet | 11.47 g | 96.3% | 11.04 g | 90% |
| B SUDAFED 30 mg Tablet w/denaturant | None | N/A | None | 0% |
| E Generic 30 mg Tablets | 12.74 g | 94.75% | 12.74 g | 98% |
| F Generic 30 mg Tablets w/denaturant | None | N/A | None | 0% |

What is claimed is:

1. A pharmaceutical composition comprising:
   a water soluble acid salt of a sympathomimetic amine; and
   a denaturant comprising (i) at least one gum or viscosity modifier, and (ii) at least one surfactant,
   wherein said gum or viscosity modifier and said surfactant are present in amounts sufficient to have a denaturing effect on said sympathomimetic amine but ineffective to provide sustained release of said sympathomimetic amine from the composition.

2. The composition according to claim 1, wherein said surfactant is a poly(oxypropylene)poly(oxyethylene) copolymer.

3. The composition according to claim 2, wherein said poly(oxypropylene)poly(oxyethylene) copolymer has the formula $HO(C_2H_4O)_{101}(C_3H_6O)_{56}(C_2H_4O)_{101}H$.

4. The composition according to claim 1, wherein said gum or viscosity modifier is a polyethylene oxide compound.

5. The composition according to claim 1, wherein said surfactant is a poly(oxypropylene)poly(oxyethylene) copolymer and said gum or viscosity modifier is a polyethylene oxide compound.

6. The composition according to claim 5, wherein said poly(oxypropylene)poly(oxyethylene) copolymer has the formula $HO(C_2H_4O)_{101}(C_3H_6O)_{56}(C_2H_4O)_{101}H$.

7. The composition according to claim 1, wherein said surfactant comprises at least one ionic surfactant and at least one non-ionic surfactant.

8. The composition according to claim 7, wherein said gum or viscosity modifier is a polyethylene oxide compound.

9. The composition according to claim 7, wherein said ionic surfactant is sodium lauryl sulfate.

10. The composition according to claim 7, wherein said non-ionic surfactant is a poly(oxypropylene)poly(oxyethylene) copolymer.

11. The composition according to claim 10, wherein said poly(oxypropylene)poly(oxyethylene) copolymer has the formula $HO(C_2H_4O)_{101}(C_3H_6O)_{56}(C_2H_4O)_{101}H$.

12. The composition according to claim 7, wherein said gum or viscosity modifier is a polyethylene oxide compound, said non-ionic surfactant is a poly(oxypropylene)poly(oxyethylene) copolymer and said ionic surfactant is sodium lauryl sulfate.

13. A method of physically interfering with the extraction of a water soluble acid salt of a sympathomimetic amine from a pharmaceutical composition containing said acid salt of a sympathomimetic amine, comprising physically interfering with the extraction of the acid salt of a sympathomimetic amine from a pharmaceutical composition by incorporating in said pharmaceutical composition a denaturant comprising at least one pharmaceutically and biologically acceptable gum or viscosity modifier and at least one surfactant, said gum or viscosity modifier and surfactant being present in amounts sufficient to interfere with the extraction of said sympathomimetic amine but ineffective to provide sustained release of said sympathomimetic amine from said composition.

14. The method according to claim 13, wherein said surfactant is a poly(oxypropylene)poly(oxyethylene) copolymer.

15. The method according to claim 14, wherein said poly(oxypropylene)poly(oxyethylene) copolymer has the formula $HO(C_2H_4O)_{101}(C_3H_6O)_{56}(C_2H_4O)_{101}H$.

16. The method according to claim 13, wherein said gum or viscosity modifier is a polyethylene oxide compound.

17. The method according to claim 13, wherein said at least one surfactant is a poly(oxypropylene)poly(oxyethylene) copolymer and said gum or viscosity modifier is a polyethylene oxide compound.

18. The method according to claim 17, wherein said poly(oxypropylene)poly(oxyethylene) copolymer has the formula $HO(C_2H_4O)_{101}(C_3H_6O)_{56}(C_2H_4O)_{101}H$.

19. The method according to claim 13, wherein said surfactant comprises at least one ionic surfactant and at least one non-ionic surfactant.

20. The method according to claim 19, wherein said gum or viscosity modifier is a polyethylene oxide compound.

21. The method according to claim 19, wherein said ionic surfactant is sodium lauryl sulfate.

22. The method according to claim 19, wherein said non-ionic surfactant denaturant is a poly(oxypropylene)poly(oxyethylene) copolymer.

23. The method according to claim 22, wherein said poly(oxypropylene)poly(oxyethylene) copolymer has the formula $HO(C_2H_4O)_{101}(C_3H_6O)_{56}(C_2H_4O)_{101}H$.

24. The method according to claim 19, wherein said gum or viscosity modifier is a polyethylene oxide compound, said non-ionic surfactant is a poly(oxypropylene)poly(oxyethylene) copolymer and said ionic surfactant is sodium lauryl sulfate.

25. A pharmaceutical composition comprising;
   a water soluble acid salt of a sympathomimetic amine; and
   a denaturant comprising polyethylene oxide in an amount sufficient to have a denaturing effect on said sympathomimetic amine but ineffective to provide sustained release of said sympathomimetic amine from the composition.

26. The composition according to claim 25, further comprising at least one surfactant.

27. The composition according to claim 26, wherein the surfactant comprises a poly(oxypropylene)poly(oxyethylene) copolymer.

28. The composition according to claim 27, wherein the poly(oxypropylene)poly(oxyethylene) copolymer has the formula $HO(C_2H_4O)_{101}(C_3H_6O)_{56}(C_2H_4O)_{101}H$.

29. The composition according to claim 26, wherein the surfactant comprises at least one ionic surfactant and at least one non-ionic surfactant.

30. The composition according to claim 29, wherein the ionic surfactant is sodium lauryl sulfate.

31. The composition according to claim 29, wherein the non-ionic surfactant is a poly(oxypropylene)poly(oxyethylene) copolymer.

32. The composition according to claim 29, wherein the ionic surfactant is sodium lauryl sulfate and the non-ionic surfactant is a poly(oxypropylene)poly(oxyethylene) copolymer.

33. A method of physically interfering with the extraction of a water soluble acid salt of a sympathomimetic amine from a pharmaceutical composition containing said acid salt of a sympathomimetic amine, comprising physically interfering with the extraction of the acid salt of a sympathomimetic amine from a pharmaceutical composition by incorporating in said pharmaceutical composition a denaturant comprising polyethylene oxide in an amount sufficient to interfere with the extraction of said sympathomimetic amine but ineffective to provide sustained release of said sympathomimetic amine from said composition.

34. The method according to claim 33, wherein the pharmaceutical composition further comprises at least one surfactant.

35. The method according to claim 34, wherein the surfactant comprises a poly(oxypropylene)poly(oxyethylene) copolymer.

36. The method according to claim 35, wherein the poly(oxypropylene)poly(oxyethylene) copolymer has the formula $HO(C_2H_4O)_{101}(C_3H_6O)_{56}(C_2H_4O)_{101}H$.

37. The method according to claim 34, wherein the surfactant comprises at least one ionic surfactant and at least one non-ionic surfactant.

38. The method according to claim 37, wherein the ionic surfactant is sodium lauryl sulfate.

39. The method according to claim 37, wherein the non-ionic surfactant is a poly(oxypropylene)poly(oxyethylene) copolymer.

40. The method according to claim 37, wherein the ionic surfactant is sodium lauryl sulfate and the non-ionic surfactant is a poly(oxypropylene)poly(oxyethylene) copolymer.

* * * * *